United States Patent
Nordstrom et al.

(10) Patent No.: US 6,760,613 B2
(45) Date of Patent: *Jul. 6, 2004

(54) SUBSTANTIALLY MONOSTATIC, SUBSTANTIALLY CONFOCAL OPTICAL SYSTEMS FOR EXAMINATION OF SAMPLES

(75) Inventors: Robert Nordstrom, Hanover, MA (US); Mark Modell, Natick, MA (US); Alexander Zelenchuk, Stoughton, MA (US)

(73) Assignee: MediSpectra, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/178,772
(22) Filed: Jun. 24, 2002

(65) Prior Publication Data

US 2002/0183626 A1 Dec. 5, 2002

Related U.S. Application Data

(63) Continuation of application No. 09/470,071, filed on Dec. 12, 1999, now Pat. No. 6,411,838.
(60) Provisional application No. 60/113,761, filed on Dec. 23, 1998.

(51) Int. Cl.[7] .............................................. A61B 6/00
(52) U.S. Cl. ...................... 600/476; 600/407; 600/473; 600/478
(58) Field of Search ......................... 600/476, 407, 600/473, 478, 474, 475, 425

(56) References Cited

U.S. PATENT DOCUMENTS

| | | | |
|---|---|---|---|
| 3,013,467 A | 12/1961 | Minsky | 88/14 |
| 3,632,865 A | 1/1972 | Haskell et al. | 178/6 |
| 3,809,072 A | 5/1974 | Ersek et al. | 128/23 |
| 3,890,462 A | 6/1975 | Limb et al. | 178/6.8 |
| 3,963,019 A | 6/1976 | Quandt et al. | 128/2 |

(List continued on next page.)

FOREIGN PATENT DOCUMENTS

| | | |
|---|---|---|
| EP | 0 135 134 | 3/1985 |
| EP | 0 280 418 | 8/1988 |
| EP | 0 335 725 | 10/1989 |
| EP | 0 444 689 A2 | 9/1991 |
| EP | 0 474 264 | 3/1992 |

(List continued on next page.)

OTHER PUBLICATIONS

Agrawal et al. (1999), "Fluorescence Spectroscopy of the Cervix: Influence of Acetic Acid, Cervical Mucus, and Vaginal Medications," *Lasers in Surgery and Medicine*, 25:237–249.

(List continued on next page.)

*Primary Examiner*—Eleni Mantis Mercader
(74) *Attorney, Agent, or Firm*—Testa, Hurwitz & Thibeault, LLP

(57) ABSTRACT

The present invention relates to systems and methods for examining a sample using a substantially monostatic, substantially confocal optical system comprising transmitting optics that focus an illuminating light upon the sample and receiving optics that collect light emitted from the sample following illumination thereof. In certain embodiments, the receiving optics may be arranged circumferentially around the light path traversed by the illuminating light. In certain embodiments, video apparatus may be included to produce images or to align the system in proximity to the target tissue. The systems and methods of the present invention may be directed towards the examination of a body tissue to provide a medical diagnosis.

19 Claims, 6 Drawing Sheets

U.S. PATENT DOCUMENTS

| | | |
|---|---|---|
| D242,393 S | 11/1976 | Bauman |
| D242,396 S | 11/1976 | Bauman |
| D242,397 S | 11/1976 | Bauman |
| D242,398 S | 11/1976 | Bauman |
| 4,017,192 A | 4/1977 | Rosenthal et al. .......... 356/201 |
| 4,071,020 A | 1/1978 | Pugliese et al. ................ 128/2 |
| 4,198,571 A | 4/1980 | Sheppard ..................... 250/571 |
| 4,218,703 A | 8/1980 | Netravali et al. ........... 358/136 |
| 4,254,421 A | 3/1981 | Kreutel, Jr. .................. 343/754 |
| 4,273,110 A | 6/1981 | Groux ............................. 128/6 |
| 4,357,075 A | 11/1982 | Hunter ........................ 350/294 |
| 4,397,557 A | 8/1983 | Herwig et al. ............... 356/342 |
| 4,549,229 A | 10/1985 | Nakano et al. ................. 360/8 |
| 4,646,722 A | 3/1987 | Silverstein et al. ............. 128/4 |
| 4,662,360 A | 5/1987 | O'Hara et al. .................. 128/9 |
| 4,733,063 A | 3/1988 | Kimura et al. ............... 250/201 |
| 4,741,326 A | 5/1988 | Sidall et al. .................... 128/4 |
| 4,753,530 A | 6/1988 | Knight et al. ................. 356/73 |
| 4,768,513 A | 9/1988 | Suzuki ....................... 128/634 |
| 4,800,571 A | 1/1989 | Konishi ....................... 375/10 |
| 4,844,617 A | 7/1989 | Kelderman et al. ......... 356/372 |
| 4,845,352 A | 7/1989 | Benschop ................... 250/201 |
| 4,852,955 A | 8/1989 | Doyle et al. .................. 350/1.2 |
| 4,877,033 A | 10/1989 | Seitz, Jr. ................. 128/660.05 |
| 4,878,485 A | 11/1989 | Adair ............................. 128/6 |
| 4,891,829 A | 1/1990 | Deckman et al. .............. 378/4 |
| 4,930,516 A | 6/1990 | Alfano et al. ................ 128/665 |
| 4,945,478 A | 7/1990 | Merickel et al. ........ 364/413.22 |
| 4,965,441 A | 10/1990 | Picard ..................... 250/201.3 |
| 4,972,258 A | 11/1990 | Wolf et al. .................... 358/93 |
| 4,974,580 A | 12/1990 | Anapliotis .................... 128/4 |
| 4,979,498 A | 12/1990 | Oneda et al. ................... 128/6 |
| 4,997,242 A | 3/1991 | Amos ........................ 350/6.91 |
| 5,003,979 A | 4/1991 | Merickel et al. ........ 364/413.22 |
| 5,011,243 A | 4/1991 | Doyle et al. .................. 350/1.2 |
| 5,022,757 A | 6/1991 | Modell ........................ 356/318 |
| 5,028,802 A | 7/1991 | Webb et al. .................. 250/571 |
| 5,032,720 A | 7/1991 | White ......................... 250/236 |
| 5,034,613 A | 7/1991 | Denk et al. ................ 250/458.1 |
| 5,036,853 A | 8/1991 | Jeffcoat et al. .............. 128/634 |
| 5,042,494 A | 8/1991 | Alfano ........................ 128/665 |
| 5,048,946 A | 9/1991 | Sklar et al. .................. 351/206 |
| 5,054,926 A | 10/1991 | Dabbs et al. ................ 356/345 |
| 5,065,008 A | 11/1991 | Hakamata et al. .......... 250/216 |
| 5,071,246 A | 12/1991 | Blaha et al. .................. 351/221 |
| 5,074,306 A | 12/1991 | Green et al. ................. 128/664 |
| 5,083,220 A | 1/1992 | Hill .............................. 359/234 |
| 5,091,652 A | 2/1992 | Mathies et al. ........... 250/458.1 |
| 5,101,825 A * | 4/1992 | Gravenstein et al. ........ 600/326 |
| 5,120,953 A | 6/1992 | Harris ...................... 250/227.2 |
| 5,122,653 A | 6/1992 | Ohki ........................... 250/216 |
| 5,132,526 A | 7/1992 | Iwasaki .................... 250/201.3 |
| 5,139,025 A | 8/1992 | Lewis et al. ................. 128/665 |
| 5,154,166 A | 10/1992 | Chikama ........................ 128/4 |
| 5,159,919 A | 11/1992 | Chikama ........................ 128/4 |
| 5,161,053 A | 11/1992 | Dabbs ......................... 359/384 |
| 5,162,641 A | 11/1992 | Fountain .................. 250/201.2 |
| 5,162,941 A | 11/1992 | Favro et al. .................. 359/386 |
| 5,168,157 A | 12/1992 | Kimura ....................... 250/234 |
| 5,192,980 A | 3/1993 | Dixon et al. ................. 356/326 |
| 5,193,525 A | 3/1993 | Silverstein et al. ............. 128/4 |
| RE34,214 E | 4/1993 | Carlsson et al. ............... 358/93 |
| 5,199,431 A | 4/1993 | Kittrell et al. ............... 128/634 |
| 5,201,318 A | 4/1993 | Rava et al. .................. 128/665 |
| 5,201,908 A | 4/1993 | Jones ............................. 128/4 |
| 5,203,328 A | 4/1993 | Samuels et al. ............. 128/633 |
| 5,225,671 A | 7/1993 | Fukuyama .................. 250/216 |
| 5,235,457 A | 8/1993 | Lichtman et al. ........... 359/368 |
| 5,237,984 A | 8/1993 | Williams, III et al. .......... 128/4 |
| 5,239,178 A | 8/1993 | Derndinger et al. ........ 250/234 |
| 5,248,876 A | 9/1993 | Kerstens et al. ............. 250/561 |
| 5,253,071 A | 10/1993 | MacKay ...................... 358/222 |
| 5,257,617 A | 11/1993 | Takahashi ....................... 128/4 |
| 5,260,569 A | 11/1993 | Kimura ....................... 250/234 |
| 5,260,578 A | 11/1993 | Bliton et al. .............. 250/461.1 |
| 5,261,410 A | 11/1993 | Alfano et al. ................ 128/664 |
| 5,262,646 A | 11/1993 | Booker et al. ............... 250/341 |
| 5,274,240 A | 12/1993 | Mathies et al. ........... 250/458.1 |
| 5,284,149 A | 2/1994 | Dhadwal et al. ............. 128/665 |
| 5,286,964 A | 2/1994 | Fountain .................. 250/201.2 |
| 5,289,274 A | 2/1994 | Kondo ........................ 348/208 |
| 5,294,799 A | 3/1994 | Aslund et al. ........... 250/458.1 |
| 5,296,700 A | 3/1994 | Kumagai ..................... 250/216 |
| 5,303,026 A | 4/1994 | Strobl et al. ................. 356/318 |
| 5,306,902 A | 4/1994 | Goodman ................. 250/201.3 |
| 5,313,567 A | 5/1994 | Civanlar et al. ............. 395/124 |
| 5,319,200 A | 6/1994 | Rosenthal et al. ........... 250/341 |
| 5,321,501 A | 6/1994 | Swanson et al. ............ 356/345 |
| 5,324,979 A | 6/1994 | Rosenthal ............... 250/504 R |
| 5,325,846 A | 7/1994 | Szabo ............................ 128/4 |
| 5,329,352 A | 7/1994 | Jacobsen ..................... 356/301 |
| 5,337,734 A | 8/1994 | Saab ............................. 128/4 |
| 5,343,038 A | 8/1994 | Nishiwaki et al. .......... 250/234 |
| 5,345,306 A | 9/1994 | Ichimura et al. ............ 356/346 |
| 5,345,941 A | 9/1994 | Rava et al. .................. 128/665 |
| 5,349,961 A | 9/1994 | Stoddart et al. ............. 128/665 |
| 5,398,685 A | 3/1995 | Wilk et al. ................ 128/653.1 |
| 5,402,768 A | 4/1995 | Adair ............................ 128/4 |
| 5,406,939 A | 4/1995 | Bala .............................. 128/4 |
| 5,413,092 A | 5/1995 | Williams, III et al. .......... 128/4 |
| 5,413,108 A | 5/1995 | Alfano ........................ 128/665 |
| 5,415,157 A | 5/1995 | Welcome ....................... 128/4 |
| 5,418,797 A | 5/1995 | Bashkansky et al. .......... 372/3 |
| 5,419,311 A | 5/1995 | Yabe et al. ..................... 128/4 |
| 5,419,323 A | 5/1995 | Kittrell et al. ............... 128/653 |
| 5,421,337 A | 6/1995 | Richards-Kortum et al. ............. 128/665 |
| 5,421,339 A | 6/1995 | Ramanujam et al. ....... 128/665 |
| 5,424,543 A | 6/1995 | Dombrowski et al. ...... 250/330 |
| 5,450,857 A | 9/1995 | Garfield et al. ............. 128/778 |
| 5,451,931 A | 9/1995 | Miller et al. ................. 340/630 |
| 5,458,132 A | 10/1995 | Yabe et al. ..................... 128/4 |
| 5,458,133 A | 10/1995 | Yabe et al. ................. 600/121 |
| 5,467,767 A | 11/1995 | Alfano et al. ................ 128/665 |
| 5,469,853 A | 11/1995 | Law et al. ............. 128/662.06 |
| 5,477,382 A | 12/1995 | Pernick ....................... 359/559 |
| 5,480,775 A | 1/1996 | Ito et al. ...................... 435/7.2 |
| 5,493,444 A | 2/1996 | Khoury et al. ............... 359/559 |
| 5,496,259 A | 3/1996 | Perkins ....................... 600/124 |
| 5,507,295 A | 4/1996 | Skidmore .................... 600/121 |
| 5,516,010 A | 5/1996 | O'Hara et al. .............. 600/122 |
| 5,519,545 A | 5/1996 | Kawahara ..................... 360/46 |
| 5,529,235 A | 6/1996 | Bolarski et al. ........... 227/175.1 |
| 5,536,236 A | 7/1996 | Yabe et al. .................. 600/125 |
| 5,545,121 A | 8/1996 | Yabe et al. .................. 600/121 |
| 5,551,945 A | 9/1996 | Yabe et al. .................. 600/122 |
| 5,556,367 A | 9/1996 | Yabe et al. .................. 600/124 |
| 5,562,100 A | 10/1996 | Kittrell et al. ............... 128/665 |
| 5,579,773 A | 12/1996 | Vo-Dinh et al. ............ 128/665 |
| 5,582,168 A | 12/1996 | Samuels et al. ............. 128/633 |
| 5,587,832 A | 12/1996 | Krause ........................ 359/385 |
| 5,596,992 A | 1/1997 | Haaland et al. ............. 128/664 |
| 5,599,717 A | 2/1997 | Vo-Dinh ....................... 436/63 |
| 5,609,560 A | 3/1997 | Ichikawa et al. ........... 600/101 |
| 5,612,540 A | 3/1997 | Richards-Korum et al. ........... 250/461.2 |
| 5,623,932 A | 4/1997 | Ramanujam et al. ....... 128/665 |
| 5,647,368 A | 7/1997 | Zeng et al. .................. 128/665 |
| 5,662,588 A | 9/1997 | Lida ............................ 600/121 |
| 5,685,822 A | 11/1997 | Harhen ....................... 600/125 |
| 5,690,106 A | 11/1997 | Bani-Hashemi et al. .. 128/653.1 |

| | | |
|---|---|---|
| 5,693,043 A | 12/1997 | Kittrell et al. ............... 606/15 |
| 5,695,448 A | 12/1997 | Kimura et al. ............. 600/121 |
| 5,697,373 A | 12/1997 | Richards-Kortum et al. ............. 128/664 |
| 5,699,795 A | 12/1997 | Richards-Kortum et al. ............. 128/634 |
| 5,704,892 A | 1/1998 | Adair ........................ 600/121 |
| 5,707,343 A | 1/1998 | O'Hara et al. ............. 600/121 |
| 5,713,364 A | 2/1998 | DeBaryshe et al. ......... 128/664 |
| 5,717,209 A | 2/1998 | Bigman et al. ........ 250/339.12 |
| 5,730,701 A | 3/1998 | Furukawa et al. ......... 600/127 |
| 5,733,244 A | 3/1998 | Yasui et al. ................. 600/127 |
| 5,735,276 A | 4/1998 | Lemelson et al. .......... 128/653 |
| 5,746,695 A | 5/1998 | Yasui et al. ................. 600/127 |
| 5,768,333 A | 6/1998 | Abdel-Mottaleb ........... 378/37 |
| 5,769,792 A | 6/1998 | Palcic et al. ................ 600/477 |
| 5,773,835 A | 6/1998 | Sinofsky et al. ......... 250/462.1 |
| 5,791,346 A | 8/1998 | Craine et al. ............... 128/653 |
| 5,795,632 A | 8/1998 | Buchalter .................. 428/35.2 |
| 5,800,350 A | 9/1998 | Coppleson et al. ......... 600/372 |
| 5,807,248 A | 9/1998 | Mills .......................... 600/322 |
| 5,813,987 A | 9/1998 | Modell et al. .............. 600/473 |
| 5,817,015 A | 10/1998 | Adair ........................ 600/121 |
| 5,830,146 A | 11/1998 | Skladnev et al. ........... 600/478 |
| 5,833,617 A | 11/1998 | Hayashi ..................... 600/476 |
| 5,840,035 A | 11/1998 | Heusmann et al. ........... 600/47 |
| 5,842,995 A | 12/1998 | Mahadevan-Jansen et al. ............... 600/473 |
| 5,855,551 A | 1/1999 | Sklandnev et al. ......... 600/372 |
| 5,860,913 A | 1/1999 | Yamaya et al. ............. 600/127 |
| 5,863,287 A | 1/1999 | Segawa ...................... 600/121 |
| 5,865,726 A | 2/1999 | Katsurada et al. .......... 600/127 |
| 5,876,329 A | 3/1999 | Harhen ...................... 600/125 |
| 5,920,399 A | 7/1999 | Sandison et al. ........... 356/418 |
| 5,921,926 A | 7/1999 | Rolland et al. ............. 600/407 |
| 5,929,985 A | 7/1999 | Sandison et al. ........... 365/318 |
| 5,931,779 A | 8/1999 | Arakaki et al. ............. 600/310 |
| 5,938,617 A | 8/1999 | Vo-Dinh .................... 600/476 |
| 5,941,834 A | 8/1999 | Skladnev et al. ........... 600/587 |
| 5,983,125 A | 11/1999 | Alfano et al. ............... 600/473 |
| 5,989,184 A | 11/1999 | Blair et al. ................. 600/167 |
| 5,991,653 A | 11/1999 | Richards-Kortum et al. ............. 660/475 |
| 5,995,645 A | 11/1999 | Soenksen et al. ........... 382/133 |
| 6,021,344 A | 2/2000 | Lui et al. .................... 600/476 |
| 6,058,322 A | 5/2000 | Nishikawa et al. ......... 600/408 |
| 6,069,689 A | 5/2000 | Zeng et al. ................. 356/773 |
| 6,091,985 A | 7/2000 | Alfano et al. ............... 600/476 |
| 6,095,982 A | 8/2000 | Richards-Kortum et al. ............. 600/476 |
| 6,096,065 A | 8/2000 | Crowley ...................... 607/88 |
| 6,099,464 A | 8/2000 | Shimizu et al. ............. 600/104 |
| 6,104,945 A | 8/2000 | Modell et al. .............. 600/473 |
| 6,119,031 A | 9/2000 | Crowley ..................... 600/407 |
| 6,124,597 A | 9/2000 | Shehada et al. .......... 250/461.2 |
| 6,146,897 A | 11/2000 | Cohenford et al. ........... 436/63 |
| 6,169,817 B1 | 1/2001 | Parker et al. ............... 382/131 |
| 6,208,887 B1 | 3/2001 | Clarke et al. ............... 600/476 |
| 6,241,662 B1 | 6/2001 | Richards-Kortum et al. ............. 600/310 |
| 6,243,601 B1 * | 6/2001 | Wist ........................... 600/477 |
| 6,246,471 B1 | 6/2001 | Jung et al. .................... 356/73 |
| 6,246,479 B1 | 6/2001 | Jung et al. .................. 356/419 |
| 6,285,639 B1 | 9/2001 | Maenza et al. .......... 369/47.28 |
| 6,312,385 B1 | 11/2001 | Mo et al. .................... 600/443 |
| 6,317,617 B1 | 11/2001 | Gilhuijs et al. ............. 600/408 |
| D453,832 S | 2/2002 | Morrell et al. ............. D24/138 |
| D453,962 S | 2/2002 | Morrell et al. ............. D24/138 |
| D453,963 S | 2/2002 | Morrell et al. ............. D24/138 |
| D453,964 S | 2/2002 | Morrell et al. ............. D24/138 |
| 6,377,842 B1 | 4/2002 | Pogue et al. ................ 600/478 |
| 6,385,484 B2 | 5/2002 | Nordstrom et al. ......... 600/476 |
| 6,411,835 B1 | 6/2002 | Modell et al. .............. 600/407 |
| 6,411,838 B1 | 6/2002 | Nordstrom et al. ......... 600/476 |
| D460,821 S | 7/2002 | Morrell et al. ............. D24/138 |
| 6,421,553 B1 | 7/2002 | Costa et al. ................. 600/476 |
| 6,427,082 B1 | 7/2002 | Nordstrom et al. ......... 600/476 |
| 6,571,118 B1 * | 5/2003 | Utzinger et al. ............ 600/476 |
| 6,574,502 B2 | 6/2003 | Hayashi ...................... 600/476 |
| 2002/0007123 A1 | 1/2002 | Balas et al. ................. 600/476 |

FOREIGN PATENT DOCUMENTS

| | | |
|---|---|---|
| EP | 0 641 542 | 3/1995 |
| EP | 0 689 045 A1 | 12/1995 |
| EP | 0 737 849 A2 | 10/1996 |
| JP | 08-280602 | 10/1996 |
| SU | 1 223 092 A | 4/1986 |
| WO | WO 92/19148 | 11/1992 |
| WO | WO 93/14688 | 8/1993 |
| WO | WO 94/26168 | 11/1994 |
| WO | 95/00067 | 1/1995 |
| WO | WO 95/04385 | 2/1995 |
| WO | WO 97/05473 | 2/1997 |
| WO | WO 98/30889 | 2/1997 |
| WO | WO 97/48331 | 12/1997 |
| WO | WO 98/05253 | 2/1998 |
| WO | WO 98/24369 | 6/1998 |
| WO | WO 98/41176 | 9/1998 |
| WO | WO 99/18847 | 4/1999 |
| WO | WO 99/20313 | 4/1999 |
| WO | WO 99/20314 | 4/1999 |
| WO | WO 99/47041 | 9/1999 |
| WO | WO 99/57507 | 11/1999 |
| WO | WO 99/57529 | 11/1999 |
| WO | WO 00/15101 | 3/2000 |
| WO | WO 00/59366 | 10/2000 |

OTHER PUBLICATIONS

Althof et al. (1997), "A rapid and automatic image registration algorithm with subpixel accuracy," *IEEE Transactions on Medical Imaging*, 16(3):308–316.

Anderson (1994), "Confocal Laser Microscopes See A Wider Field of Application", *Laser Focus World*, pp. 83–86.

Aström et al. (1999), "Motion estimation in image sequences using the deformation of apparent contours," *IEEE Transactions on Pattern Analysis and Machine Intelligence*, 21(2):114–127.

Balas (1997), "An Imaging Colorimeter for Noncontact Tissue Color Mapping," *IEEE Transactions on Biomedical Engineering*, 44(6):468–474.

Balas (2001), "A Novel Optical Imaging Method for the Early Detection, Quantitative Grading, and Mapping of Cancerous and Precancerous Lesions of Cervix," *IEEE Transactions on Biomedical Engineering*, 48(1):96–104.

Balas et al. (1997), "A modular diffuse reflection and fluorescence emission imaging colorimeter for the in–vivo study of parameters related with the phototoxic effect in PDT," *SPIE*, 3191:50–57.

Balas et al. (1998), "In Vivo Assessment of Acetic Acid–Cervical Tissue Interaction Using Quantitative Imaging of Back–Scattered Light: Its Potential Use for the In Vivo Cervical Cancer Detection Grading and Mapping," Part of EUROPTO Conference on Optical Biopsy, Stockholm, Sweden, *SPIE*, vol. 3568:31–37.

Balas et al. (1999), "In Vivo Detection and Staging of Epithelial Dysplasias and Malignancies Based on the Quantitative Assessment of Acetic Acid–Tissue Interaction Kinetics," *Journal of Photochemistry and Photobiology B: Biology*, 53:153–157.

Bessey et al. (1949), "The Fluorometric measurement of the nucleotides of riboflavin and their concentration in tissues," *J. Biol.–Chem.*; 180:755–769.

Bors et al. (1998), "Optical flow estimation and moving object segmentation based on median radial basis function network," *IEEE Transactions on Image Processing*, 7(5):693–702.

Bouthemy et al. (1999), "A unified approach to shot change detection and cameras motion characterization," *IEEE Transactions on Circuits and Systems for Video Technology*, 9(7):1030–1044.

Braichotte et al. (1995), "Clinical Pharmacokinetic Studies of Photofrin by Fluorescence Spectroscopy in the Oral Cavity, the Esophagus, and the Bronchi," *Cancer* 75(11):2760–2778.

Brown (1990), "Chemometrics," *Anal. Chem.*, 62:84R–101R.

Camus et al. (1997), "Real–time quantized optical flow," *Real–Time Imaging*, 3:71–86.

Caplier et al. (1998), "Real–time implementation of a MRF–based motion detection algorithm," *Real–Time Imaging*, 4:41–54.

Contini et al. (1989), "Colposcopy and Computer Graphics: a New Method?" *Amer. J. Obstet. Gynecol.*, 160(3):535–538.

Craine et al. (1993), "Digital Imaging Colposcopy: basic concepts and applications," *Amer. J. Obstet. Gynecol.*, 82(5):869–873.

Craine et al. (1998), "Digital imaging colposcopy: Corrected area measurements using shape–from–shading," *IEEE Transactions on Medical Imaging*, 17(6):1003–1010.

Crisp et al. (1990), "The Computerized Digital Imaging Colposcope: Future Directions," *Amer. J. Obstet. Gynecol.*, 162(6):1491–1497.

Cronjé et al. (1997), "Effects of Dilute Acetic Acid on the Cervical Smear," *Acta. Cytol.*, 41:1091–1094.

Davidovits et al. (1971), "Scanning Laser Microscope for Biological Invesigations", *Applied Optics*, 10(7):1615–1619.

Dickman et al. (2001), "Identification of Cervical Neoplasia Using a Simulation of Human Vision," *Journal of Lower Genital Tract Disease*, 5(3):144–152.

Drezek et al. (1999), "Light scattering from cells: finite-difference time–domain simulations and goniometric measurements," *Applied Optics* 38(16):3651–3661.

Drezek et al. (2000), "Laser Scanning Confocal Microscopy of Cervical Tissue Before and After Application of Acetic Acid," *Am. J. Obstet. Gynecol.*, 182(5):1135–1139.

Dumontier et al. (1999), "Real–time DSP implementation for MRF–based video motion detection," *IEEE Transactions on Image Processing*, 8(10):1341–1347.

Earnshaw et al. (1996), "The Performance of Camera Translation Direction Estimators from Optical Flow: Analysis, Comparison, and Theoretical Limits," *IEEE Transactions on Pattern Analysis and Machine Intelligence*, 18(9):927–932.

Edebiri, A.A. (1990), "The relative significance of colposcopic descriptive appearances in the dianosis of cervical intraepithelial neoplasia," *Int. J. Gynecol. Obstet.*, 33:23–29.

Eisner et al. (1987), "Use of Cross–Correlation Function to Detect Patient Motion During Spectral Imaging," *Journal of Nuclear Medicine*, 28(1):97–101.

Ferris et al. (1998), "Colposcopy Quality Control: Establishing Colposcopy Criterion Standards for the NCI ALTS Trial Using Cervigrams," *J. Lower Genital Tract Disease*, 2(4):195–203.

Fleet et al. (1995), "Recursive Filters for Optical Flow," *IEEE Transactions on Pattern Analysis and Machine Intelligence*, 17(1):61–67.

Gao et al. (1998), "A work minimization approach to image morphing," *The Visual Computer*, 14:390–400.

Gauch (1999), "Image Segmentation and Analysis Via Multiscale Gradient Watershed Hierarchies," *IEEE Transactions on Image Processing*, 8(1):69–79.

Hall et al. (1992), "Near–Infrared Spectrophotometry: A New Dimension in Clinical Chemistry", *Clin. Chem.* 38(9):1623–1631.

Haralick (1984), "Digital Step Edges from Zero Crossing of Second Directional Derivatives," *IEEE Transactions on Pattern Analysis and Machine Intelligence*, 6(1):58–68.

Haris et al. (1998), "Hybrid Image Segmentation Using Watersheds and Fast Region Merging," *IEEE Transactions on Image Processing*, 7(12):1684–1699.

Helmerhorst et al. (1987), "The accuracy of colposcopically directed biopsy in diagnosis of CIN 2/3." *Eur. J. Obstet. Gyn. Reprod. Biol.*, 24, 221–229.

Horn et al. (1981), "Determining Optical Flow," *Artificial Intelligence*, 17(1–3):185–203.

Horn et al. (1993), "Determining Optical Flow": a retrospective, *Artificial Intelligence*, 59:81–87.

Huang et al. (1979), "A fast two–dimensional median filtering algorithm," *IEEE Transactions on Acoustics, Speech, and Signal Processing*, 27(1):13–18.

Jackway (1996), "Gradient Watersheds in Morphological Scale–Space," *IEEE Transactions on Image Processing*, 5(6):913–921.

Ji et al. (2000), "Texture Anlaysis for Classification of Cervix Lesions," *IEEE Transactions on Medical Imaging*, 19(11):1144–1149.

Kierkegaard et al. (1995), "Association between Colposcopic Findings and Histology in Cervical Lesions: The Significance of the Size of the Lesion" *Gynecologic Oncology*, 57:66–71.

Koester (1980), "Scanning Mirror Microscope with Optical Sectioning Characteristics: Applications in Ophthalmology", *Applied Optics*, 19(11):1749–1757.

Kumar et al. (1996), "Optical Flow: A Curve Evolution Approach," *IEEE Transactions on Image Processing*, 5(4):598–610.

Linde et al. (1980), An algorithm for vector quantizer design,: *IEEE Transactions on Communications*, 28(1):84–95.

MacAulay et al. (2002), "Variation of fluorescence spectroscopy during the menstrual cycle," *Optics Express*, 10(12):493–504.

MacLean A.B. (1999), "What is Acetowhite Epithelium," *Abstract Book; 10th World Congress of Cervical Pathology and Colposcopy, Nov. 7–11*, Buenos Aires, Argentina 41.

Marzetta et al. (1999), "A surprising radon transform result and its application to motion detection," *IEEE Transactions on Image Processing*, 8(8):1039–1049.

Miike et al. (1999), "Motion enhancement for preprocessing of optical flow and scientific visualization," *Pattern Recognition Letters*, 20:451–461.

Mikhail et al. (1995), "Computerized colposcopy and conservative management of cervical intraepithelial neoplasia in pregnancy," *Acta Obstet. Gynecol. Scand.*, 74:376–378.

Milanfar (1999), "Two–dimensional matched filtering for motion estimation," *IEEE Transactions on Image Processing*, 8(3):438–444.

Mitchell et al. (1998), "Colposcopy for the diagnosis of squamous intraepithelial lesions: a meta–analysis," *Obstet. Gynecol.*, 91(4):626–631.

Mycek et al. (1998), "Colonic polyp differentiation using time–resolved autofluorescence spectroscopy," *Gastrointestinal Endoscopy*, 48(4):390–394.

Nanda et al. (2000), "Accuracy of the Papanicolaou test in screening for and follow–up of cervical cytologic abnormalities: a systematic review," *Ann Intern Med.*, 132(10):810–819.

Nesi et al. (1998), "RETIMAC REalTIme Motion Analysis Chip," *IEEE Transactions on Circuits and Systems–II: Analog and Digital Signal Processing*, 45(3):361–375.

Noumeir et al. (1996), "Detection of Motion During Tomographic Acquisition by an Optical Flow Algorithm," *Computers and Biomedical Research*, 29(1):1–15.

O'Sullivan et al. (1994), "Interobserver variation in the diagnosis and grading of dyskaryosis in cervical smears: specialist cytopathologists compared with non–specialists," *J. Clin. Pathol.*, 47(6):515–518.

Ogura et al. (1995), "A cost effective motion estimation processor LSI using a simple and efficient algorithm," *IEEE Transactions on Consumer Electronics*, 41(3):690–698.

Okatani et al. (1997), "Shape reconstruction from an endoscope image by shape from shading technique for a point light source at the projection center," *Computer Vision and Image Understanding*, 66(2):19–131.

Pan et al. (1998), "Correlation–feedback Technique in Optical Flow Determination," *IEEE Transactions on Image Processing*, 7(7):1061–1067.

Perona et al. (1990), "Scale–space and edge detection using anisotropic diffusion," *IEEE Transactions on Pattern Analysis and Machine Intelligence*, 12(7):629–639.

Pogue et al. (2001), "Analysis of Acetic Acid–Induced Whitening of High–Grade Squamous Intraepithelial Lesions," *Journal of Biomedical Optics*, 6(4):397–403.

Radjadhyaksha et al. (200), "Confocal microscopy of excised human skin using acetic acid and crossed polarization: rapid detection of non–melanoma skin cancers," *Proceedings of SPIE*, 3907:84–88.

Rakshit et al. (1997), "Computation of Optical Flow Using Basis Functions," *IEEE Transactions on Image Processing*, 6(9):1246–1254.

Ramanujam et al. (1994) "In vivo diagnosis of cervical intraepithelial neoplasia using 337–nm–excited laser–induced fluorescence", *Pro. Natl. Acad. Sci. USA*, 91:10193–10197.

Ramanujam et al. (1994), "Fluorescence Spectroscopy; A Diagnostic Tool for Cervical Intraepithelial Neoplasia (CIN)," *Gynecologic Oncology*, 52:31–38.

Reid et al. (1985), "Genital warts and cervical cancer. VII. An improved colposcopic index for differentiating benign papillomaviral infections from high–grade CIN," *Am. J. Obstet. Gynecol.*, 153(6):611–618.

Richards–Kortum et al. (1994), "Description and Performed of a Fiber–optic Confocal Fluorescence Spectrometer," *Applied Spectroscopy*, 48(3):350–355.

Romano et al. (1997), "Spectroscopic study of human leukocytes," *Physica Medica*, 13:291–295.

Ruprecht et al. (1995), "Image warping with scattered data interpolation methods," *IEEE Computer Graphics and Applications*, 37–43.

Sakuma (1985), "Quantative Analysis of the Whiteness of the Atypical Cervical Transformation Zone", *The Journal of Reproductive Medicine*, 30(10):773–776.

Schmid (1999), "Lesion Detection in Dermatoscopic Images Using Anisotropic Diffusion and Morphological Flooding," *Proceedings of the International Conference on Image Processing (ICIP–99)*, 3:449–453.

Schmid (1999), "Segmentation and Symmetry Measure for Image Analysis: Application to Digital Dermatoscopy," *Ph.D. Thesis, Swiss Federal Institute of Technology (EPFL), Signal Processing Laboratory (LTS)*.

Schmid (1999), "Segmentation of Digitized Dermatoscopic Images by 2D Color Clustering," *IEEE Transactions on Medical Imaging*, 18(2):164–171.

Schmitt et al. (1994), "Confocal Microscopy in Turbid Media", *J. Opt. Soc. Am. A*, 11(8):2225–2235.

Schmitt et al. (1994), "Interferometric Versus Confocal Techniques for Imaging Microstructures in Turbid Biological Media", *Proc. SPIE*, 2135:1–12.

Schomacker et al. (1992), "Ultraviolet Laser–Induced Fluorescence of Colonic Polyps," *Gastroenterology*, 102:1155–1160.

Schomacker et al. (1992), "Ultraviolet Laser–Induced Fluorescence of Colonic Tissue; Basic Biology and Diagnostic Potential", *Lasers in Surgery and Medicine*, 12:63–78.

Schwartz (1993), "Real–time laser–scanning Confocal ratio imaging", *American Laboratory*, pp. 53–62.

Shafarenko et al. (1997), "Automatic Watershed Segmentation of Randomly Textured Color Images," *IEEE Transactions on Image Processing*, 6(11):1530–1544.

Shafi et al. (1995), "Modern image capture and data collection technology," *Clin. Obstet. Gynecol.*, 38(3):640–643.

Sheppard et al. (1978), "Depth of Field in the Scanning Microscop", *Optics Letters*, 3(3):115–117.

Szarewski et al., (1996), "Effect of smoking cessation on cervical lesions size," *Lancet*, 347:941–943.

Szeliski et al. (1997), "Spline–based image registration," *International Journal of Computer Vision*, 22(3):199–218.

Tadrous (2000), "Methods for Imaging the Structure and Function of Living Tissues and Cells: 2. Fluorescence Lifetime Imaging," *Journal of Pathology*, 191(3):229–234.

Thirion et al. (1999), "Deformation analysis to detect and quantify active lesions in three–dimensional medical image sequences," *IEEE Transactions on Medical Imaging*, 18(5):429–441.

Toglia et al. (1997), "Evaluation of colposcopic skills in an obstetrics and gynecology residency training program," *J. Lower Gen. Tract. Dis.*, 1(1):5–8.

Treameau et al. (1997), "A Region Growing and Merging Algorithm to Color Segmentation," *Pattern Recognition*, 30(7):1191–1203.

Van den Elsen et al. (1995), "Automatic registration of ct and mr brain images using correlation of geometrical features," *IEEE Transactions on medical imaging*, 14(2):384–396.

Vernon (1999), "Computation of Instantaneous Optical Flow Using the Phase of Fourier Components," *Image and Vision Computing*, 17:189–199.

Vincent et al. (1991), "Watersheds in Digital Spaces: An Efficient Algorithm Based on Immersion Simulations," *IEEE Transactions on Patterns Analysis and Machine Intelligence*, 13(6):583–598.

Vincent et al. (1993), "Morphological grayscale reconstruction in image analysis: Applications and efficient algorithms," *IEEE Transactions on Image Processing*, 2(2):176–201.

Wang et al. (1999), "Fast algorithms for the estimation of motion vectors," *IEEE Transactions on Image Processing*, 8(3):435–438.

Weng et al. (1997), "Three–Dimensional Surface Reconstruction Using Optical Flow for Medical Imaging," *IEEE Transactions on Medical Imaging*, 16(5):630–641.

Wolberg et al. (1998) "Image morphing: a survey," *The Visual Computer*, 14:360–372.

You et al. (1996), "Behavioral analysis of anisotropic diffusion in image processing," *IEEE Transactions on Image Processing*, 5(11):1539–1553.

Zahm et al. (1998), "Colposcopic appearance of cervical intraepithelial neoplasia is age dependent," *Am. J. Obstet. Gynecol.*, 179(5):1298–1304.

Zeger et al. (1992), "Globally optimal vector quantizer design by stochasic relaxation," *IEEE Transactions on Signal Processing*, 40(2):310–322.

Zeng et al. (1993), "A computerized autofluorescence and diffuse reflectance spectroanalyser system for in vivo skin studies," *Phys. Med. Biol.*, 38:231–240.

Zeng et al. (1997), "Optimization of fast block motion estimation algorithms," *IEEE Transactions on Circuits and Systems for Video Technology*, 7(6):833–844.

Zhang et al. (1999), "Shape from shading: a survey," *IEEE Transactions on Pattern Analysis and Machine Intelligence*, 21(8):690–706.

Zheng et al. (1991), "Estimation of illumination direction, albedo, and shape from shading," *IEEE Transactions on Pattern Analysis and Machine Intelligence*, 13(7):680–702.

Zhengfang et al. (1998), "Identification of Colonic Dysplasia and Neoplasia by Diffuse Reflectance Spectroscopy and Pattern Recognition Techniques," *Applied Spectroscopy*, 52(6):833–839.

* cited by examiner

SUBSTANTIALLY MONOSTATIC, SUBSTANTIALLY CONFOCAL OPTICAL SYSTEMS FOR EXAMINATION OF SAMPLES

CROSS-REFERENCE TO RELATED APPLICATIONS

This application is a continuation of U.S. patent application Ser. No. 09/470,071, filed Dec. 12, 1999, now U.S. Pat. No. 6,411,838, issued Jun. 25, 2002, which application is incorporated herein in its entirety by reference, and which application claims priority to and the benefit of U.S. provisional patent application Serial No. 60/113,761, filed Dec. 23, 1998.

FIELD OF THE INVENTION

This invention relates to the delivery of excitation light to a target tissue and the collection of response light therefrom for spectral analysis.

BACKGROUND OF THE INVENTION

Optical methods are being used with increasing frequency to determine the composition and state of samples. In particular, the use of optical techniques is growing in the medical arts for the diagnosis of tissue health in-vivo. In some instances, a beam of light is used to illuminate the tissue in a specific region, causing excitation of said tissue. Light emitted by the tissue is then collected by the receiving device and analyzed to determine the physical health of the tissue.

Two methods are known in the art that deliver and receive illumination from a designed region of tissue. In the first method, termed bistatic, the illuminating beam is focused on the sample from one direction, and light that is backscattered or emitted from the sample is received by an optical system located in a position different from the position of the delivery system. In the second method, termed monostatic, the illuminating beam path and the receiver beam path lie along the same line of sight. Such an optical scheme is also called confocal if the location of the sample is at the focal point of both the illumination optical system and the receiver optical system of the device.

According to the bistatic method for examining a sample, the field of illumination from the source and the field of view of the receiver are aligned so as to overlap at the sample, while illumination and viewing take place at different locations. Certain limitations are understood to accompany bistatic methods. For example, when this method is employed with an illuminating device that does not directly contact the sample, it is sensitive to misalignments of the device to the sample, so that any error in the distance of the non-contact device from the tissue may result in significant decrease in the amount of light collected by the receiver.

Bistatic optical probes may have illumination and receiving sections sufficiently separated from each other that the optical paths from the sample to each section are oriented along different directions. The effect of this optical design is that the illumination path and the receiving path form two sides of a triangle, intersecting in a single localized region. The surface of the sample may then be positioned in this overlap region. For some applications, this triangulation can be exploited. The receiver section may be configured to collect a signal only when the proper distance from the probe to the sample is achieved. In this embodiment, when the receiver section of the probe is detecting a signal, the distance from the probe to the sample can be known. This embodiment may lend itself to greater ease of analysis and probe calibration.

For many applications, however, the bistatic configuration is not useful. For example, contours to the sample may cause shadowing of the response from the surface of the sample to the receiver, or may cause the overlap of the receiver line of sight and the illumination line of sight to fall off of the surface. The monostatic optical design may overcome these problems. It is furthermore understood that misalignment problems can be overcome by use of a monostatic optical configuration. Additionally, if the monostatic optical configuration is also confocal, the optical receiver will collect only the light from the illuminated region on the sample.

In one embodiment of a monostatic device, the illuminating beam of light may be transmitted through a beamsplitter before it interacts with the sample. The light emitted by the sample returns to the beamsplitter, where it is reflected toward a receiver system in the device. If the illuminating excitation beam and the returned emission from the sample occupy different regions of the electromagnetic spectrum, the beamsplitter can be a dichroic mirror, with high transmission at the excitation wavelengths and high reflectivity at the sample emission wavelengths. This offers the possibility for high efficiency of optical throughput in the device. If, however, the spectral regions for the excitation and emission beams have significant overlap, the dichroic mirror cannot be used, and significant losses of optical signal can occur. In the case where the excitation and emission spectral regions are identical, the optimum beamsplitter will transmit only 50% of the excitation signal, and will reflect only 50% of the returned signal emitted by the sample. The overall efficiency of such a device is only 25%.

Another limitation of the use of a beamsplitter in the path of the excitation and emission beams is the possibility that light can be directly scattered from the illumination side to the receiver side of the probe without interaction with the sample. This can create large optical signals containing no information about the sample.

It is understood in the art that probes are available for multispectral imaging of a sample. A probe may comprise a housing and beam splitting apparatus within the housing, designed for imaging. Such a probe may not address the problem of scattering from the beam splitting surface and the level of interference this scatter will cause.

It is well known in the art that optical interrogation of samples may permanently alter the nature of the sample as a result of the measurement. Laser-induced fluorescence studies of samples, for example, temporarily alter the physical nature of the molecules in the sample. This alteration produces molecules in excited energy states that liberate optical radiation as they relax to the more favorable ground energy state. Chemical and biological changes in specific samples can also be created to liberate an optical response from the sample. An example of a permanent change in the sample is seen in laser breakdown spectroscopy, where a portion of the surface of the sample is ablated by the intense laser beam. The ablated material is in the form of an excited plasma that liberates light distinctive of the composition of the sample.

While some changes in the physical, chemical, or biological condition of the sample can be important for creating a response to the illumination, certain other changes in the sample that may be caused by an optical system or a probe may interfere with the desired measurement. For example, it is known from spectroscopic studies of in-vivo tissue that hemoglobin content can have diagnostic significance. Optical probes that contact the tissue can alter the flow of blood to the tissue, thereby altering the hemoglobin spectral feature. Such changes in sample characteristics adversely affect the ability of the optical device to measure the sample characteristics correctly. Contact of the probe with the target tissue may cause other relevant changes in the signals emitted from the tissue following illumination.

Probes in the art are known that identify tissue which is suspected of being physiologically changed as a result of pre-cancerous or cancerous activity by contacting the tissue, using separate optical fibers for transmitting the excitation light and receiving the emitted light, or using other conduits to direct heat, electrical, sound, or magnetic energy towards a target tissue. These devices rely upon contact with the tissues to derive their data, and do not embody a non-contact system for identifying tissue abnormalities.

Non-contact optical probes may be configured so they do not alter a sample in the same way as contact probes. Non-contact methods are particularly attractive in medical in-vivo diagnostic instrumentation because they do not perturb the tissue being investigated and because they do not carry the risk of contamination of the measurement site. However, non-contact probes can suffer from other limitations, most notably problems with alignment and focus. For proper operation, the two main components to the probe, namely the illumination section and the receiving section, must be aligned to the same location on the sample, and both must be in focus at the same time. Non-contact probes are known in the art that comprise systems for confocal illumination of a surface without including an apparatus for eliminating the scattered light from being transmitted from the transmitter portion to the receiver portion directly in the probe when a monostatic arrangement is used.

Therefore, there remains a need in the art for a confocal optical system that optimizes the retrieval of the emitted light from a sample after illumination in a monostatic configuration. There exists a further need to embody this system in a probe that does not require contact with the sample being illuminated. There exists an additional need for a non-contact probe that can measure the distance to the target tissue and that is adapted for optimal positioning with respect to the target tissue. No system exists presently in the art that permits an accurate non-contact technique of monostatic illumination of a sample without the potential of interference from scattered light from the components of the illumination probe. Additionally, when such optical probes are used in confined spaces, as is the case when illuminating in-vivo cervical tissue, the optical probe often obscures the common viewing of the tissue. Therefore, there is a further need to provide supplemental ability to view the target tissue during placement of the probe and during optical illumination.

SUMMARY OF THE INVENTION

It is desirable that an optical probe be provided for identifying light emission responses from a sample subjected to illumination. It is further desirable that the optical probe not interfere with physiological or morphological characteristics of the sample being examined, nor that the probe impede the ability of an optical system to detect identifying features of the response from the sample. If, for example, a desired response includes spectroscopic information (light intensity as a function of wavelength), the probe will advantageously be constructed so it will not contribute excessive spectroscopic detail to the signal. Similarly, if a desired response from the sample includes spatially related data, the optical probe will advantageously provide sufficient imaging quality to permit the identification of spatial components of the response.

In one embodiment, the present invention may comprise a probe bearing one or a plurality of lenses or mirrors for the purpose of bringing the illuminating light to a focus on the surface of the sample. The transmitting optics may occupy the center region of a cylindrical geometry. Surrounding the transmitter optics in this embodiment may be an annular optical arrangement for receiving emitted light from the sample. According to this embodiment, the emitted light returned to the probe passes through an optical system containing components different from the optical components used to form and direct the illuminating beam toward the sample, while remaining aligned to the same line of sight as the illuminating beam.

In one embodiment, the annular receiver optical system may be designed so that it accepts light emitted from the focused spot on the sample defined by the location of the illumination focal point. The emitted light from the sample collected by the probe receiver optics may then be brought to a focus elsewhere in the system for detection of for transport to a means of detection. This point of focus in the probe may be the active element of a detector, or may be the face of a fiber or fiber bundle, designed to conduct the light to another location in the device where the detection will take place. The terms receiving and collecting optics, as used herein, are understood to be interchangeable. Furthermore, the receiving optics are understood to collect, to receive and to retrieve light: all of the foregoing three terms are interchangeable, as they are used herein.

Because no single optical component is used in both the transmitter and the receiver portions of the device, the opportunity for scattered radiation from the illuminating source to enter the receiver portion of the device without first having interacted with the sample is greatly diminished, as compared to the technique of using a beamsplitter within the optical path. Care must be taken to account for light reflected from optical surfaces such as lens surfaces. This form of stray light can contaminate the measurement of the surface by passing directly from the illumination portion to the receiver portion of the probe without interacting with the sample. Practitioners of the art are familiar with baffles and stops to prevent this level of stray light contamination in the final signal.

In a particular embodiment, the sample being interrogated by the optical beam is in-vivo tissue. It is known in the art that when tissue is illuminated at a spatially limited point (e.g. 1-mm diameter spot) by a collimated beam of light, the emitted response from the tissue is in two parts. The first is a specular reflection from the surface, and is governed by Fresnel reflection created by the change in index of refraction between the air and the tissue. The second is a diffused reflection caused by the entrance of the light into the tissue where it migrates randomly before escaping the surface. It is known that this diffused reflection can occur over a wide angle from the surface. In some cases, this diffused component is modeled as having equal amounts of light in all angles measured from the perpendicular to the surface.

When the placement of the probe is critical to the quality of the measurement, and when the use of the probe is in confined spaces such as is the case when viewing in-vivo cervical tissue, it is useful to augment the operator's viewing ability of the target. This may be accomplished by means of a video camera mounted directly in the probe. The optical system for the direction and focus of the illuminating beam can also serve as the optical system to create an image of the surface of the sample for the video camera.

In one aspect, the present invention provides a system for examining a sample that includes an optical probe with a plurality of optical fibers capable of illuminating a sample, and a substantially monostatic, substantially confocal optical system comprising transmitting optics to illuminate a sample and receiving optics to collect light emitted from the sample. In certain embodiments, the system may include a reflective optical component or a refractive optical components. The system may further comprise an optical system that focuses illuminating light on a surface of the sample and that collects light emitted from the focus point. In one embodiment, the receiving optics of the system may be configured circumferentially around a light path followed by the illuminating light. In one embodiment, the system may provide a scanner that directs illuminating light towards the sample by sequentially illuminating individual optical fibers in a preselected pattern, such as a rectilinear array or a hexagonal pattern. The illuminating light may include a pulsed laser or a nitrogen laser and the emitted light may include fluorescence or Raman scattered light. The illuminating light may include broadband light, for example from a Xenon lamp, and the emitted light may include elastic backscattered light.

In one aspect, the present invention provides a system for determining a characteristic of a sample that includes an optical probe for monostatic, confocal examination of the sample; an optics system that includes transmitting optics to focus an illuminating light on the sample and receiving optics to collect light emitted from the sample; a measuring system that produces quantitative data related to the light emitted from the sample; and a processor that processes the quantitative data to determine the characteristic of the sample. The system may further include a video system to display an image of the surface of the sample. The system may further include a position sensor to determine the position of the optical probe in relation to the sample. The position sensor may provide a focusing image that is projected upon a surface of the sample, whereby the position of the optical probe in relation is determined by the clarity of focus of the focusing image.

In another aspect, the present invention provides an optical probe system for the monostatic, confocal examination of a sample, including an optical probe, a light source that produces an illuminating light, transmitting optics that focus the light on a sample, collecting optics arranged substantially as an annulus surrounding a light path for the illuminating light that collect light emitted from the sample, and a connecting circuit that transmits electromagnetic energy related to the emitted light to a processor for further processing. The system may include a scanning system that sequentially illuminates a plurality of optical fibers to pass a point of illumination over the surface of the sample in a preselected pattern. The system may further include a video channel for viewing the surface of the sample and for determining the location of the probe relative to the sample. The video channel may share an optical path with the illuminating light. The system may include a video camera dimensionally adapted for mounting on an optical probe.

In another aspect, the present invention provides a method for examining a sample, including the steps of providing a monostatic, confocal optical probe with transmitting optics and collecting optics wherein the collecting optics are disposed around a circumference of a light path for transmitting an illuminating light towards the sample; determining an optimal position for the probe in relation to the sample and placing the probe in that position; illuminating the sample with a light beam transmitted through the transmitting optics; and collecting light emitted from the sample as a result of the illumination. The method may include the step of processing electromagnetic energy related to the collected light to derive data related thereto. The method may further include creating a graphic image to represent the data related to the light collected. The method may include directing a focusing image towards the sample to determine the optimal position of the probe in relation to the sample.

In another aspect, the present invention provides a method for diagnosing a medical condition, comprising the steps of providing a monostatic, confocal optical probe comprising transmitting optics and collecting optics wherein the collecting optics are disposed around a circumference of a light path for transmitting an illuminating light toward a body tissue; illuminating the body tissue; collecting light emitted from the body tissue; measuring a set of data related to the light collected from the body tissue; and diagnosing from the set of data the medical condition. The method may further include processing the set of data with a processor. The method may further include creating a graphical image that represents the set of data.

In another aspect, the present invention provides a method of treating a medical condition, including the steps of providing a monostatic, confocal optical probe capable of illuminating a body tissue and capable of collecting therefrom emitted light, illuminating the body tissue, collecting emitted light from the body tissue, measuring a set of data related to the light emitted from the body tissue, diagnosing from the set of data the medical condition, formulating a treatment plan based on a diagnosis of the medical condition, and treating the medical condition according to the treatment plan.

In another aspect, the present invention provides a system for examining a body tissue, including an optical probe that directs an illuminating light towards the body tissue and that collects light emitted from the body tissue; a substantially monostatic, substantially confocal optical system comprising transmitting optics that focus the illuminating light on the body tissue and receiving optics that collect light emitted from the body tissue; and a measuring system that produces quantitative data related to the light emitted from the body tissue. In one embodiment, the body tissue is the cervix uteri.

In another aspect, the present invention provides a system for evaluating a medical condition in a patient, including an optical probe that directs an illuminating light towards a body tissue and that collects light emitted from the body tissue; a substantially monostatic, substantially confocal optical system comprising transmitting optics that focus the illuminating light on the body tissue and receiving optics that collect light emitted from the body tissue; a measuring system that produces quantitative data related to the light emitted from the body tissue; a processor for processing quantitative data to derive diagnostic data related to the medical condition of the patient; and a database wherein the diagnostic data related to the medical condition of the patient may be stored. In one embodiment, the database may also store the patient's medical record. In another embodiment, the system may include a tracker to record procedure data from the procedure wherein the system is used to evaluate the medical condition of the patient. The tracker may store procedure data in the database. The database may further comprise billing information, and the system may further relate billing information to the procedure data.

In another aspect, the present invention provides a method for delivering a health care service, including the steps of storing a medical record of a patient in a database; collecting billing information related to the patient; evaluating a body tissue of the patient with an optical system comprising an optical probe for monostatic, confocal examination of the body tissue using an illuminating light focused on the body tissue by transmitting optics and using a collection system for retrieving light emitted by the body tissue after illumination; processing the light emitted by the body tissue to produce a diagnosis of a medical condition of the patient; entering the diagnosis in the medical record; and relating the diagnosis to the billing information to generate a bill. The method may further include the step of recording procedure data in the database for the procedure of evaluating the body tissue. The method may further include the step of relating the procedure data to the billing information to generate a second bill for the health care service.

These and other features of the systems and methods of the present invention will become more readily apparent to those skilled in the art from the following detailed description of certain illustrative or preferred embodiments thereof.

BRIEF DESCRIPTION OF THE FIGURES

For a more complete understanding of the nature and objects of the invention, reference should be made to the following detailed description and accompanying drawings.

Figure 1:
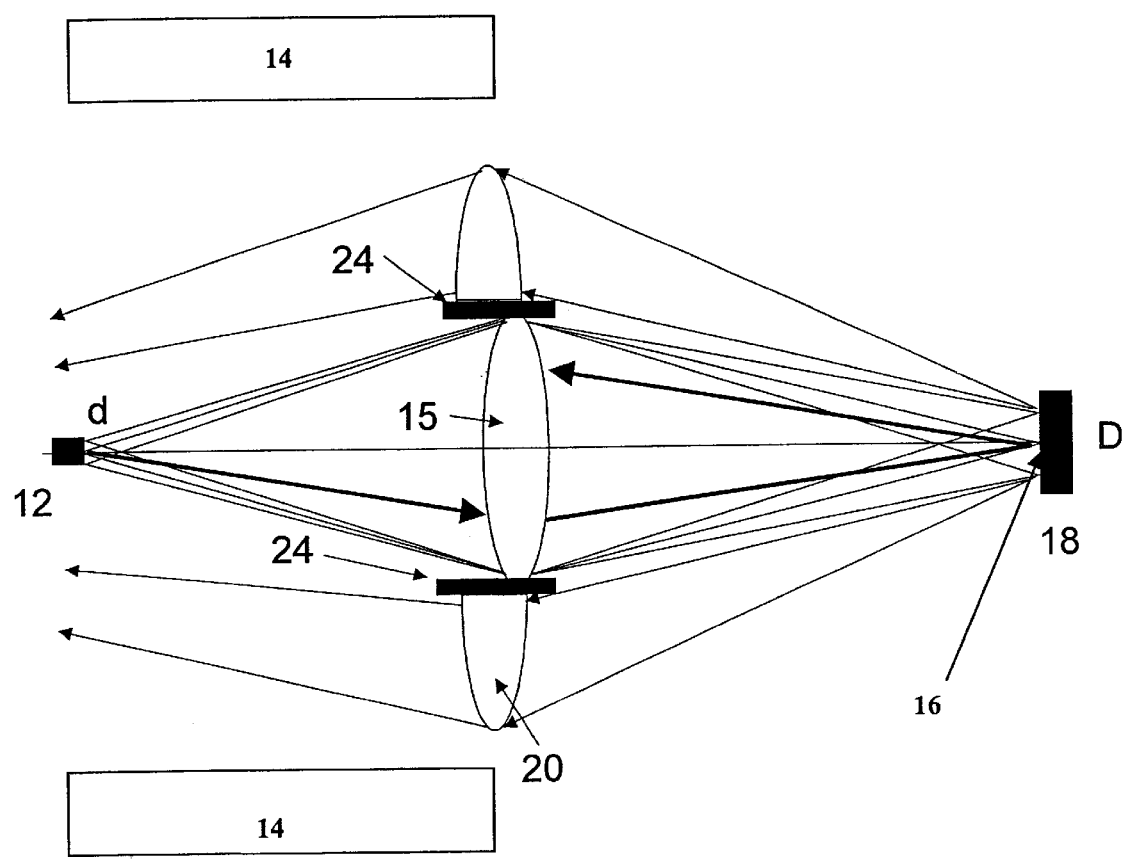
FIG. 1 provides a schematic diagram of an embodiment of an optical probe

The foregoing and other objects, features and advantages of the present invention will be apparent from the following more particular description of illustrative embodiments of the invention, as illustrated by the accompanying figures in which like reference characters refer to the same parts throughout the different views. The drawings are not necessarily to scale, emphasis being placed instead upon illustrating the principles of the invention.

DETAILED DESCRIPTION OF THE FIGURES

FIG. 1 shows a schematic cross-section of one embodiment of the optical probe 10 according the invention. A housing 14 having a proximal and a distal end is shown in this figure as enclosing the optical components. The distal end of the housing may be most remote from the operator or closest to the target sample. While a housing 14 is shown in the embodiment depicted in FIG. 1, it is understood that an optical probe may be constructed according to these systems and methods wherein the optical elements are not enclosed as a single housing. Other arrangements combining elements for illuminating a sample and for collecting light from the sample after its illumination may be readily envisioned by practitioners of ordinary skill in these arts, and certain of these arrangements are depicted in the embodiments illustrated in the following figures.

FIG. 1 further shows refractive optics 15 internal to the probe forming a focus 16 of the illuminating light on the surface of the sample 18. The source of the illuminating light 12 may be the end of a fiber of diameter d and numerical aperture $Na_f$. The diameter of the optical elements and the placement of these elements relative to the end of the fiber are such that the light exiting the fiber is entirely collected by the optical elements and directed to a focal point of diameter D on the surface of the sample. The measure of D may be greater than, less than, or equal to the measure of d. The magnification of the illuminating optics is then said to be D/d. Other configurations of illumination systems may be envisioned by or familiar to ordinarily skilled practitioners of these arts.

In this and all other figures of this disclosure, the optical system for the illumination and receiving sections of the probe are each drawn, for illustrative purposes, as comprising a single lens. It is understood that embodiments of the probe may be constructed that bear collections or arrays of lenses configured for different purposes, and that these additional embodiments are specifically contemplated by the systems and methods of the present invention.

While the light paths shown in FIG. 1 illustrate a single beam of illuminating light, it is understood that a plurality of optical fibers providing illuminating light may be illuminated in a sequential manner to create a pattern of illuminating light directed to the target. The order in which the fibers are illuminated may be predetermined in order to form a particularly advantageous pattern of illumination on the target. A scanning system may be included in these systems and methods to direct the sequence of fiber illumination. Patterns of illumination and sequencing of optical fibers to attain those patterns may be readily envisioned by those of ordinary skill in the relevant arts.

In FIG. 1, the receiver optics 20 is shown to be shaped in an annular fashion around the central illuminating optical path. While an annulus is depicted here, practitioners of ordinary skill in the art will appreciate that any geometric shape arranging the receiver optics circumferentially around a central illuminating axis may be substituted as embodiments falling within the scope of the present invention. In the illustrated embodiment, the optic axis for the receiver optics is the same as the optic axis for the illuminating optics. A baffle or barrier 24 may optically separate the illuminating section of the optics from the receiving section. This barrier may prevent stray light from entering the receiver optics 20 directly from the illuminating portion of the probe.

In the embodiment illustrated in FIG. 1, the component of the illuminating light that is specularly reflected (i.e., wherein the angle of reflection equals the angle of incidence) from the surface of the sample 18 is not directed into the receiver section when the distal surface of the probe is normal to the line of sight (or symmetry axis) of the probe. This specular component of the reflection may be collected by the illuminating optics, rather than the receiver optics. As a result, the specular component may not be detected by the detector. Diffusely reflected light from the surface, however, can occur at angles other than the angle of incidence. Thus, a portion of this diffusely reflected light may be collected by the annular optical receiver optics and brought to a focus within the body of the probe.

Other spectroscopic methods such as fluorescence and Raman spectroscopy benefit from the fact that the specularly reflected component of the excitation beam is not collected by the receiver optics 20. In the fluorescence technique, for example, a laser may be used to illuminate the sample at a specific wavelength. The light emitted from the sample as a result of the excitation by the laser beam may be produced by physical or chemical components of the sample. In one embodiment, emitted light may be observed at wavelengths longer than the wavelength of the excitation beam, but shorter wavelengths can also be investigated. The specularly reflected laser beam tends to be more intense than the fluorescence signal, and may constitute unwanted radiation in fluorescence experiments. An embodiment of a probe as illustrated in FIG. 1 may significantly reduce the amount of specularly reflected laser light entering the receiver portion, thus reducing the unwanted signal generated by the laser.

It is understood that fluorescence emitted by an illuminated sample does not retain the degree of collimation and wavelength purity of the illuminating laser beam. In most cases, fluorescence can be considered to be nearly isotropic, that is, that all directions for the fluorescence emission are equally probable. Therefore, fluorescence from a sample may be similar to diffuse reflectance, with light propagating into all possible angles from the surface. Also, the intensity of the fluorescence emitted from most samples can be very weak compared to the illuminating beam. The receiver section of the probe may thus be advantageously designed to collect a maximum amount of the emitted light from the sample in fluorescence applications. This may be accomplished by making the annular receiver area as large as possible, and by selecting optical coatings for the components that match the optical bandwidth of the fluorescence signal.

Figure 2:
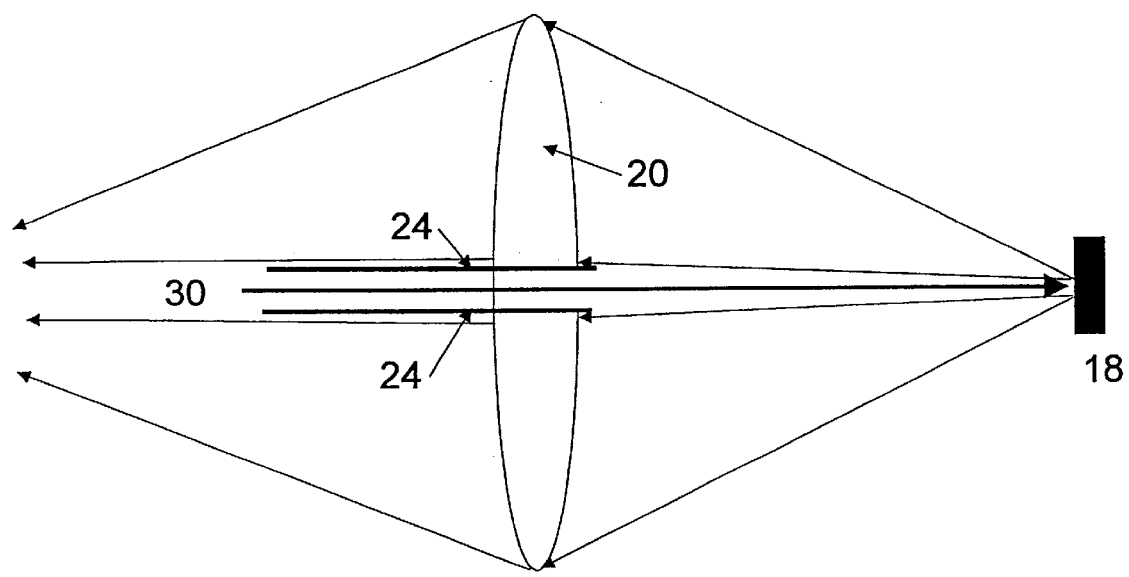
FIG. 2 provides a schematic diagram of an embodiment of an optical probe employing a laser for illumination.

FIG. 2 depicts an embodiment wherein the illuminating laser beam is sufficiently well collimated that precise illuminating optics may become optional. In this figure, a laser beam 30 passes straight through the probe without alteration by an optical system. In the depicted embodiment, the illuminating portion of the probe occupies the area between the two optical barriers 24 that separate the illuminating portion from the receiver optics 20. Use of a well collimated laser reduces the area occupied by the illuminating portion of the probe, creating a greater overall area for the receiver optics 20. An embodiment like that shown in FIG. 2 is particularly well adapted for fluorescence studies of samples.

Information concerning the physical, chemical, or biological nature of a sample can be communicated through the diffusely reflected portion of the reflected light from the surface. This is especially true of biological tissue, where a portion of the illuminating light enters the tissue and undergoes scattering and absorption before exiting the tissue. Through this process, the propagation direction of the light is randomized, becoming diffusely reflected rather than specularly reflected. In addition, information regarding the sample is imparted to the light beam, especially through the spectrum of the diffusely reflected beam. Diffuse reflectance from other samples such as soils, chemical powders, polymer surfaces, textiles, etc. contains information on the chemical composition of the sample.

For some applications of the optical probe, it may be advantageous to balance the amount of light delivered to the sample and the amount of light collected by the receiver portion. This balancing may be desirable, for example, when a broadband white light is used to interrogate the sample by creating a diffused reflectance spectrum of the sample. In such a situation, a useful design may provide an area of the illumination optics and an area of the receiving optics that are equal. For example, if the overall probe diameter is P, the diameter of the inner portion (the illuminating section in this embodiment) will be P/2 to achieve the equal areas in the receiver and illumination sections. An embodiment showing these features is illustrated in FIG. 3.

Figure 3:
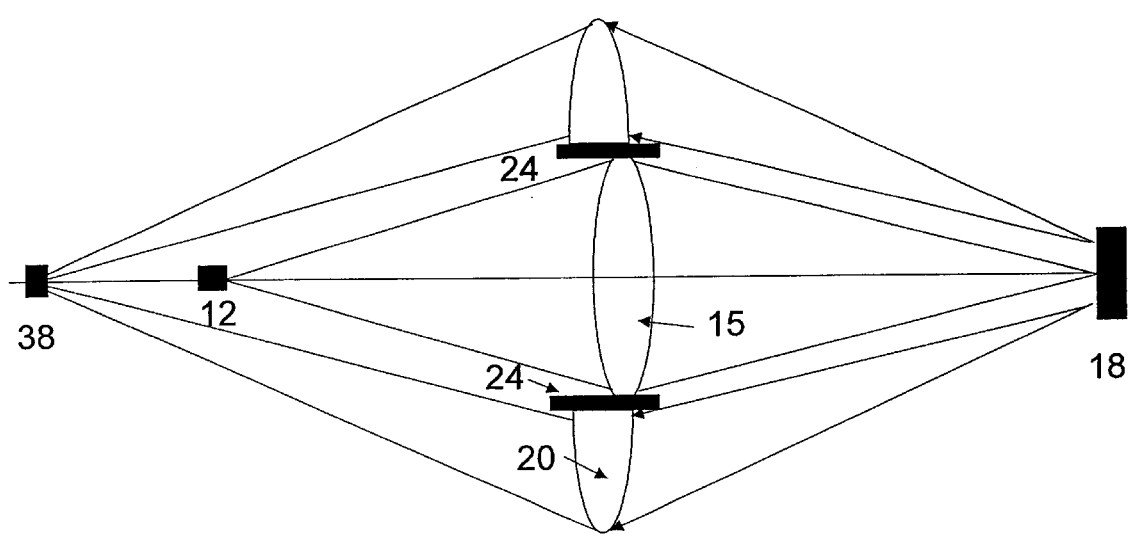
FIG. 3 provides a schematic diagram of an embodiment of an optical probe wherein the optical transmission and receiving paths are substantially equal.

FIG. 3 depicts an embodiment wherein the light collected by the receiver portion of the probe may be brought to a focus 38 at some distance from the collecting optics. In the illustrated embodiment, the location of this focus 38 is within the body of the probe. To avoid overlap of this point with the source of illuminating light 12, a number of options may be available that are consistent with the monostatic design. In one embodiment, the focal length of the receiving optics 20 may be longer than the focal length of the illumination optics. This will cause the location of the receiver focal spot 38 to fall at a greater distance from the optical system than the distance of the source from the same optical system. The result is the ability of the received light to pass around the location of the source and form a focal spot. This focal spot 38 may advantageously coincide with the location of a detecting element. Alternatively, the focal spot 38 may coincide with the location of a fiber end or a fiber bundle end adapted for transmitting received light to another location for detection. Similarly, it could be the location of a fiber end or fiber bundle end designed to transmit the received light to another location for detection. It is understood that any type of optical transducer, photodetector or phototransistor may be suitable for positioning at or near the focal spot to collect, measure or generate a signal in response to the focused light.

Because the receiver optical element or elements are arranged in a circumferential array around the illuminating beam in the depicted embodiment, the central portion of the conical beam coming to a focus, 38, is obscured. This may allow the received beam to pass around the illuminating source 12 without losses.

Figure 4:
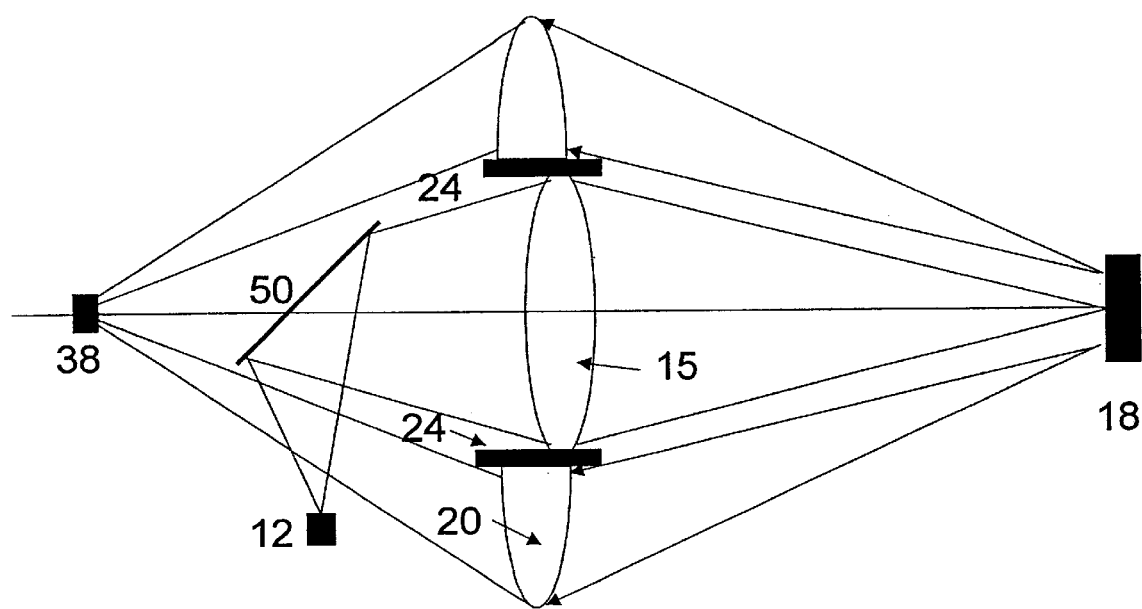
FIG. 4 provides a schematic diagram of an embodiment of an optical probe showing the presence of a turning mirror.

FIG. 4 depicts an alternative embodiment not comprising the use of unequal focusing dimensions. In the illustrated embodiment, a small turning mirror 50 can be inserted into the illuminating beam path before the focusing lens 15 is encountered by the beam. This mirror 50 allows the illuminating source 12 to be placed away from the point at which the received light is brought to a focus 38 by the receiving lenses 24.

Figure 5:
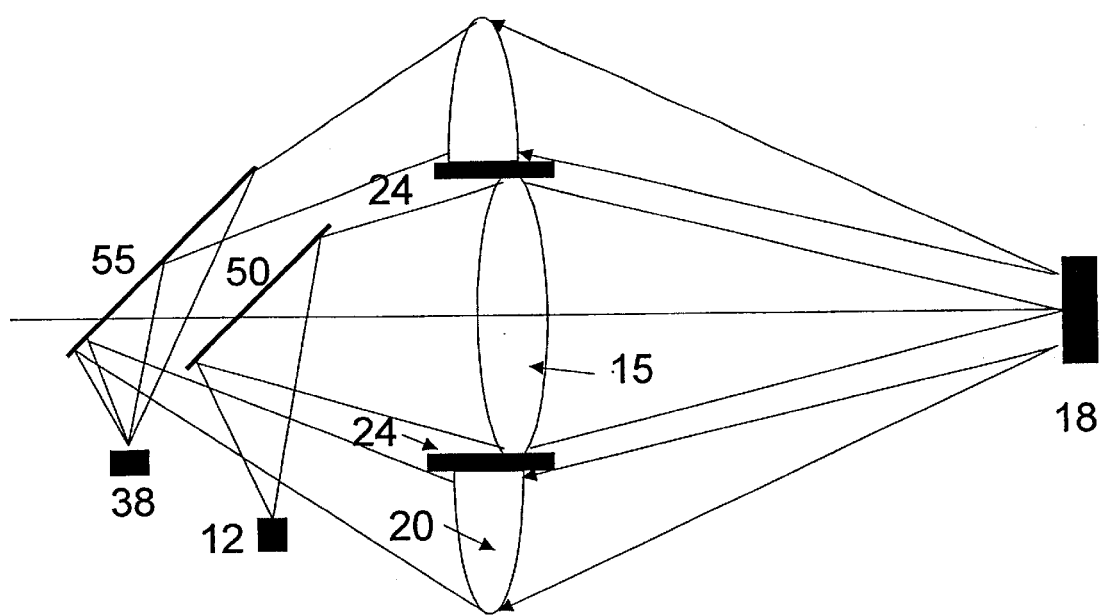
FIG. 5 provides a schematic diagram of an embodiment of an optical probe showing the presence of two turning mirrors.

FIG. 5 depicts an embodiment wherein the operation of the optical probe 10 may advantageously employ an angular design instead of a straight design. In the depicted embodiment, a mirror 50 can be used to deflect the illuminating light from illuminating source 12, and a mirror 55 can be used to deflect the received light and direct it to a focus 38.

Figure 6:
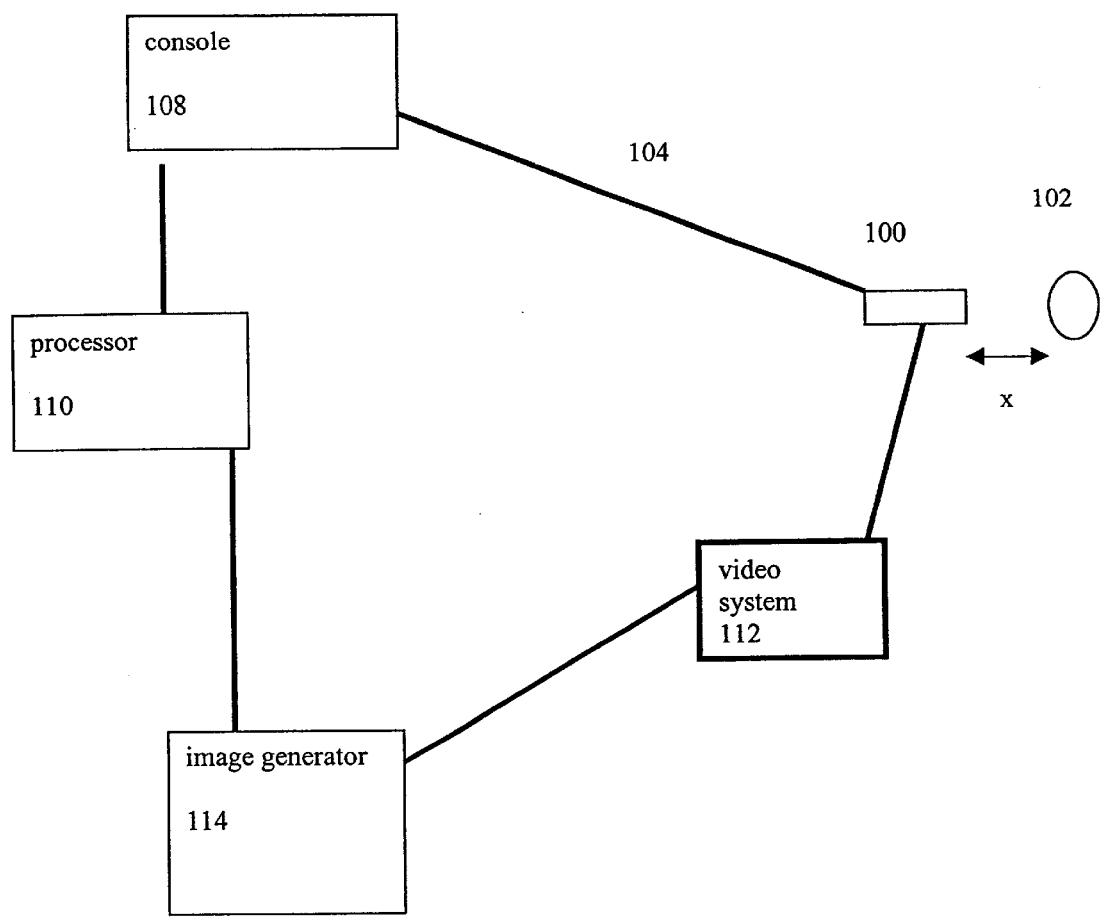
FIG. 6 provides a functional block diagram of a system for examining a sample according to the present invention.

FIG. 6 shows a functional block diagram of an embodiment of a system according to the present invention. This figure shows an optical probe 100 directed towards a sample 102. A distance x exists between the distal end of the probe 100 and the sample 102. In one embodiment, the optical probe 100 may contain all of the components necessary to generate the desired illuminating light and to convert the received light from the sample into electrical signals. Such a probe may be termed self-contained. In another embodiment, the optical probe 100 may receive transmitted light from a console 108 to which it is operably connected, or may transmit light received within the optical probe 100 to the console 108. Such a probe may be termed remote-operated.

If the optical fibers are used for transmitting light to and from the optical probe 100, the generation of the illuminating light can take place in the console 108. This light is carried to the optical probe 100 through the fibers within the connecting circuit 104, where it is then formed by the optics in the probe 100 to come to a focus on the sample 102. Similarly, when optical fibers are used, the collected light from the sample 102 can be focused on the end of a fiber or bundle of fibers and transmitted to the console 108 for detection. If the connection to the console 108 is through electrical wires only, the generation of the illuminating light and the detection of the light emitted by the sample 102 must be done in the probe 100.

A remote-operated probe, furthermore, may be directed in three dimensional space via signals transmitted from an operator who directs the positioning of the optical probe 100 with respect to the sample 102 by inputting data into the console 108. The optical probe 100 is operably connected to the console 108 by a connecting circuit 104, a conduit that may bear optical fibers, electrical wires or other conductors adapted for transmitting electromechanical energy. The connecting circuit 104 may in some embodiments include systems for radiofrequency transmission. The connecting circuit 104 provides a connection between the console 108 and the optical probe 100, so that an operator may direct the functioning of the probe during the illumination of the sample 102 and during the collection of light emitted by the sample 102.

This arrangement depicted in FIG. 6 allows for the direction of the probe 100 to examine samples at a considerable distance from the site of the console 108 and the operator. An embodiment of a probe could be directed, for example, to examine samples in locations inaccessible to human investigators. For example, a probe could be affixed to a catheter system for use within a body lumen or a channel bearing body fluids. A probe could also be adapted for insertion into small orifices such as Eustachian tubes or nasopharyngeal or sinus passages. A probe could also be adapted for geological or industrial purposes, to be placed in small crevices or within structures. A probe could be adapted for use in hostile environments, including areas contaminated with infectious agents, toxins or radiation, and including inhospitable macroenvironments such as undersea use or extraterrestrial use. Other embodiments of an optical probe according to these systems and methods may be devised that are suitable for various other environments and applications, as will be envisioned by skilled practitioners in the relevant arts.

Optical instruments used to interrogate the physical, chemical, or biological state of a sample may involve a method for delivering specific, known qualities of light to the sample, and collecting the response light from the sample for detection and analysis. In one embodiment, an optical probe 100 may be incorporated in a system for delivering the required light to the sample 102, and for collecting the resulting response for analysis. In certain embodiments, the optical probe 100 may be designed to be hand-held. It may furthermore be designed to withstand extremes in environmental conditions such as temperature or pressure. It may contain all of the required components necessary to make the optical measurement of the sample, or it may be connected to a console unit in which the requisite measurement components are housed. The connecting circuit 104 may comprise electrical, optical or other electromechanical components.

Data related to light emitted from the sample 102 may be manipulated within a processor 110 so that other data sets related to the emitted light may be obtained. Data may further be displayed in a graphical format on an image generator 114. The optical probe 100 may, in certain embodiments, bear a video camera adapted for transmitting signals to a video system 112. The video system 112 may be configured to produce digital data related to the images of the sample 102 transmitted from the optical probe 100. These digital data may be transmitted to the image generator 114 to be displayed graphically, or to be combined with other graphic representations to produce a composite graphical image.

In one practice of these methods, the optical probe 100 may be brought into proximity to the sample 102. Proper operating distance x from the sample may advantageously be established in a number of ways. In one embodiment, the distance x from the sample 102 to the optical probe 100 can be measured, or can be fixed using a rod of known length. If this is not possible, however, other methods for determining the proper operating distance can be used.

In one embodiment, an optical method for distance control may be used wherein a visible grid or array of multiple spots on the sample may be generated from an auxiliary light source in the console or in the probe. According to this embodiment, the grid may be projected through the optics in the probe onto the target. When the grid is in focus, the probe 100 is understood to be at the correct distance x from the sample 102.

Proper focus of the confocal device may be judged by the quality of the focus presented in the video image, or it may be augmented by specific focusing aids. An example of a focusing aid comprises a projected grid or series of spots on the target. In this example, gross motion of the probe towards or away from the target will bring the grid or spots into sharp focus, as viewed through the video channel. Fine adjustment of the focus can be made as in a camera, by the adjustment of the optical system delivering and receiving the light.

In another embodiment, an array of visible spots may be generated on the sample 102 by illuminating fibers in a fiber bundle located in the probe 100, using, for example, a small laser situated in the console or in the probe. The pattern of fibers in the bundle may be brought to a focus on the target sample 102 by the optics in the optical probe 100. According to this embodiment, when the spots are all in focus, the probe 100 is in the proper position relative to the sample 102. With a number of spots distributed over the surface of the sample 102, angular errors such as tilt of the probe can be eliminated when the correct focus is set for each of the spots.

Other methods for determining whether the probe 100 is situated at the proper distance x from the sample 102 will be readily apparent to those of ordinary skill in these arts. Technologies related to radar, sonar, ultrasound or GPS may be adapted in certain embodiments to the measurement of the distance x between the probe 100 and the sample 102.

A video viewing capability may be useful to confirm proper focus of the sample and proper alignment of the probe to the sample. A video viewing capability may be advantageously employed when the optical probe is used in confining spaces, or where access to the probe during operation is difficult or impossible. The video camera may furthermore permit the operator to position the probe for proper focus in relation to the sample. Viewing the focusing grid or spots may be accomplished through the optical configuration of the probe 100, allowing an operator to confirm the accuracy of the focus of the probe's optics upon the sample. This feature may be provided by means of a video camera mounted in the probe 100.

In an alternate embodiment, a beam splitter (not shown) may be provided in the transmitting beam path to combine a video capability with the diagnostic capability of the probe. The beam splitting element may align the viewing direction with the direction of the illuminating beam being transmitted to the sample. When the combination of the video and diagnostic functions in the probe occurs before the illuminating light passes through the beam-forming optics, it is possible to use the video image to determine proper focus of the illuminating beam on the sample. This can be done by directly viewing the illumination spots on the sample, if the illumination occurs within the band of visible wavelengths. If this is not the case, an aid to focusing is provided by supplying an illumination grid or series of spots in the form of an array covering the area of the sample.

With the video camera sharing its optical path with the illuminating portion of the probe, the generation of the focusing grid or spots may take place in the receiver section of the device. That is, the receiver optics may be used to project the focusing grid or spot array onto the sample. By thus using the receiver portion of the probe to create the illumination of the focusing spots, a measure of the receiver focus may be provided along with the visual realization of the illuminating focus offered by the video camera. Thus the location of the probe for optimum focus of both the transmitting and receiving portions of the probe may be determined.

In certain embodiments the probe 100 is suitable for examination of a sample 102 that includes a body tissue. A body tissue may include an in vivo or an ex vivo tissue sample. A body tissue may include any tissue of a living body, whether external or internal. Body tissues may be accessed via endoscopes, probes, specula, open surgical techniques or any other method familiar to practitioners in the relevant arts. Other approaches to body tissues suitable for the present invention will be apparent to those of ordinary skill in the medical arts. The examination of a body tissue may yield a diagnosis of a medical condition. A medical condition may comprise any physiological or pathological state of relevance to the health or wellbeing of a human subject. Medical conditions include both normal and abnormal conditions, and further include an entire spectrum of abnormalities. Examples of medical conditions include neoplasms, malignancies, dysplasias, inflammation, infection, endocrine disorders, metabolic disorders, vascular abnormalities, reparative processes, regenerative processes, degenerative processes and other conditions affecting the health or well-being of the subject. Data related to the systems and methods of the present invention may be processed to yield information about medical conditions and diagnoses. In one embodiment, data collected from the examination of a body tissue of a patient may be compared to known data profiles for known medical conditions or diagnoses, so that a diagnosis may be established for the patient. In another embodiment, normal and abnormal levels may be established for certain data points or data sets, so that the presence or absence of disease may be established by comparing the data points or data sets obtained from the examination of a patient's body tissue with the established parameters. After establishing a diagnosis according to these systems and methods, the present invention further provides for the establishment of a treatment plan based thereupon. The diagnosed medical condition may then be treated according to the treatment plan. According to these systems and methods, data related to the examination of the patient may be correlated with other data in the patient's medical record.

In another embodiment, the systems and methods of the present invention may collect data pertaining to the examination procedure itself. The system according to the present invention may measure and record information about the duration of the procedure, the amount of energy or other consumable supplies utilized to perform the procedure, the number of measurements taken during the procedure, or any other features of the procedure of significance. In one embodiment, the procedure and its duration may be tallied and correlated with patient information so that an appropriate bill for the service may be constructed. Billing information may be entered into a database that can then be accessed by the system to produce a bill for the particular procedure. In certain embodiments, the billing information may include a diagnostic or a procedural code for categorizing the procedure so that a bill bearing this information may be generated that will then be associated with a schedule of predetermined fees. Diagnosis according to ICD-9 codes and procedural terminology according to CPT codes are well-known in the art. Other codes or categories may be used for organizing a patient's billing information, so that each procedure according to these systems and methods will generate an accurate bill. Billing information may differ from one patient to the next according to the fee schedules for various managed care organizations and third-party payors. In one embodiment, the systems and methods of the present information may comprise the entry of billing information for a particular patient into a database. The billing information may then be correlated with data about the procedure itself or with data about the diagnosis produced in order to generate an accurate bill. Although the embodiments described herein relate to the application of these systems and methods to the diagnosis and treatment of medical conditions and to the delivery of health care services, it is understood that these systems and methods may be directed to the examination of any target, and that these systems and methods may furthermore be correlated with systems for recording data that identifies characteristics of the target so that outcomes of the examination may be usefully stored in relation to other data pertaining to the target.

While this invention has been particularly shown and described with reference to certain illustrated embodiments thereof, it will be understood by those skilled in the art that various changes in form and details may be made therein without departing from the scope of the invention encompassed by the appended claims.

What is claimed is:

1. A system for examining a sample, comprising:
   an optical probe capable of illuminating a sample;
   a substantially monostatic, substantially confocal optical system comprising
      transmitting optics that direct illumination upon the sample, and
      receiving optics, comprising components separate and distinct from the transmitting optics, that collect light emitted from the sample following illumination thereof; and
   a barrier element adapted to inhibit scattered illumination from entering the receiving optics.

2. The system of claim 1, further comprising reflective optical components.

3. The system of claim 1, further comprising refractive optical components.

4. The system of claim 1, wherein the optical system directs illumination at a location in the sample and wherein the optical system collects light emitted as a result of illumination from said location.

5. The system of claim 1, wherein the receiving optics are arranged circumferentially around a light path for the illumination.

6. The system of claim 1, further comprising a scanner that directs the illumination to illuminate the sample in a preselected pattern.

7. The system of claim 6, wherein the preselected pattern comprises a rectilinear pattern.

8. The system of claim 6, wherein the preselected pattern comprises a hexagonal pattern.

9. The system of claim 1, wherein the illumination comprises laser light and wherein the light emitted from the sample comprises fluorescence.

10. The system of claim 1, the illumination is provided by a broadband source and the emitted light comprises elastic backscattered light.

11. The system of claim 1, wherein the illumination is provided by a pulsed laser and the emitted light comprises Raman scattered light.

12. The system of claim 1, wherein the illumination comprises light from a nitrogen laser.

13. The system of claim 1, wherein the illumination comprises light from a Nd:YAG laser, tripled in output frequency to a wavelength of 355 nm.

14. The system of claim 1, wherein the illumination comprises broadband light provided by a xenon lamp.

15. The system of claim 1, further comprising a measuring system that produces quantitative data related to the light emitted from the sample.

16. The system of claim 15, further comprising a processor that processes the quantitative data to determine the characteristic of the sample.

17. The system of claim 15, further comprising a video system, wherein the video system transmits to a display an image of a surface of the sample.

18. The system of claim 15, further comprising a position sensor whereby a position of the optical probe in relation to the sample may be determined.

19. The system of claim 18, wherein the position sensor comprises a focusing image projected upon the surface of the sample, whereby the position of the optical probe in relation to the sample is determined by evaluating clarity of focus for the focusing image.

* * * * *